United States Patent [19]

Jurgutis

[11] Patent Number: 4,592,346
[45] Date of Patent: Jun. 3, 1986

[54] ORTHOPEDIC STAPLE

[76] Inventor: John A. Jurgutis, 506 Georgina Ave., Santa Monica, Calif. 90402

[21] Appl. No.: 721,207

[22] Filed: Apr. 8, 1985

[51] Int. Cl.⁴ .............................................. A61F 2/28
[52] U.S. Cl. .............................. 128/92 B; 128/334 R; 411/457; 411/470; 411/461
[58] Field of Search ................ 128/92 R, 92 B, 92 C, 128/334 R; 411/457, 461–467, 470

[56] References Cited

U.S. PATENT DOCUMENTS

| | | | |
|---|---|---|---|
| 431,175 | 7/1890 | Southwick | 411/470 |
| 2,058,020 | 10/1936 | Jaffe | 411/457 |
| 3,479,919 | 11/1969 | Lidsky | 411/470 |
| 3,896,500 | 7/1975 | Rambert et al. | 128/92 B |
| 4,229,888 | 10/1980 | Rawson | 411/470 |
| 4,454,875 | 6/1984 | Pratt et al. | 128/334 R |

OTHER PUBLICATIONS

Richards Mfg. Co., Memphis, Tenn., 11-15-1974.

Primary Examiner—Gene Mancene
Assistant Examiner—John G. Weiss
Attorney, Agent, or Firm—Stuart O. Lowry

[57] ABSTRACT

The staple comprises a top having four downwardly depending legs adjacent to its four corners. Two of the downwardly depending legs on the same side of the top are spaced inwardly from the corners relative to the remaining two legs so as to be transversely offset therefrom. The offset legs avoid the risk of splitting the bone when the staple bridges the bone "grain". In other words, the two legs will enter different cleavage planes of the bone rather than the same cleavage plane. Projections are provided on the underside of the top of the staple to aid in frictionally gripping and retaining a tendon or equivalent tie being held by the staple to a bone.

8 Claims, 10 Drawing Figures

ORTHOPEDIC STAPLE

FIELD OF THE INVENTION

This invention relates generally to orthopedics and more particularly to an improved staple for use in securing a tendon, ligament, or equivalent tie to a bone.

BACKGROUND OF THE INVENTION

In ligament replacement operations it is common practice to use staples for securing the ends of a tendon or equivalent tie to bone surfaces. These staples may take the form of simple U-shaped pieces of metal similar to paper staples except that they are generally of greater thickness and strength. In some instances, the staples may comprise a top with four depending legs at the four corners of the top thereby providing a four-prong staple.

One problem encountered with the use of orthopedic staples of the above type, particularly the four-prong staple, is the driving in of two of the legs in the same cleavage plane or "grain direction" of the bone. In this respect, the situation is similar to the driving of two nails in alignment with a grain of wood which has a tendency to split the wood. The same result can occur in a bone if the staple legs are in alignment with a cleavage plane; that is, fall in the same plane. In this respect, the cleavage planes of a bone are similar to the "grain" of wood. Splitting of the bone results in a weakened gripping of the staple legs and a possibility of the tendon or other tie becoming disconnected from the bone as a result of pulling out of the staple.

In other situations, even where a staple is firmly imbedded in the bone, there can still occur a pulling out or disconnection of the ligament or equavelant tie from the staple. In this respect, tension on the ligament can ultimately pull the stapled end out from beneath the top of the staple.

Orthopedic staples of the two-prong type are shown in my U.S. Pat. No. 4,467,478, issued Aug. 28, 1984 which patent is concerned with a human ligament replacement.

BRIEF DESCRIPTION OF THE PRESENT INVENTION

Bearing all of the foregoing in mind, the present invention contemplates the provision of an improved orthopedic staple of the four-prong type which substantially overcomes the above problems.

More particularly, and in its broadest aspect, the staple of the present invention comprises a rectangular top having front and rear longitudinal edges and left and right transverse edges. Integrally formed downwardly depending front legs are provided adjacent to the front corners at opposite ends of the front longitudinal edge of the top. Integrally formed downwardly depending rear legs, in turn, are provided spaced inwardly of the rear corners at opposite ends of the rear longitudinal edge of the top so as to be transversely offset from the front legs.

As a consequence of the foregoing construction, bridging the bone grain with a staple so that the longitudinal edges of the top are at right angles to the grain minimizes the risk of splitting of the bone when driving the legs of the staple into the bone.

In the present specification and claims, the term "grain" applied to a bone is meant to define the direction of "cleavage planes" of the bone which are analogous to the grain in wood.

BRIEF DESCRIPTION OF THE DRAWINGS

The foregoing features as well as many further advantages and features of the present invention will be better understood by referring to the accompanying drawings in which.

DETAILED DESCRIPTION OF THE PREFERRED EMBODIMENT

Figure 1:
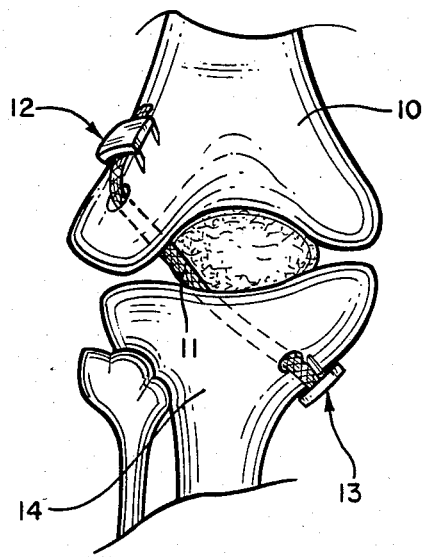
FIG. 1 is a fragmentary perspective view of a portion of a human knee illustrating the staple of the present invention used in securing the ends of a ligament in the knee.

Referring first to FIG. 1, there is shown by way of example, part of a knee bone 10. A ligament 11 has a first end secured to the bone 10 by a staple 12. Staple 12 is constructed in accord with the present invention to provide for a very secure fastening of the end of the ligament 11 to the bone 10.

Similarly, the other end of the ligament 11 is secured by a staple 13 also designed in accord with the present invention to a bone portion 14.

Figure 2:
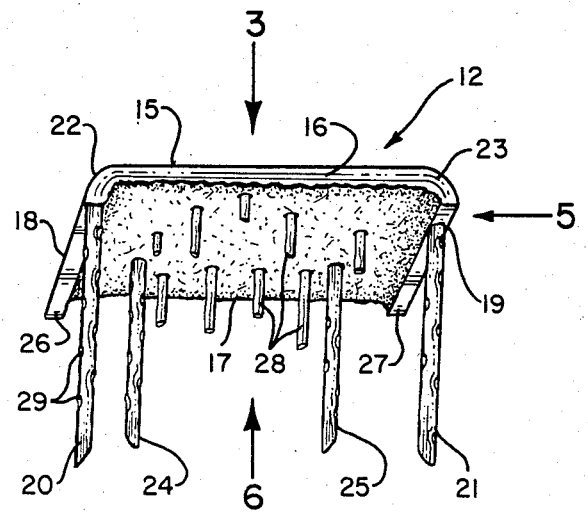
FIG. 2 is an enlarged perspective view of one of the staples of FIG. 1.
Figure 3:
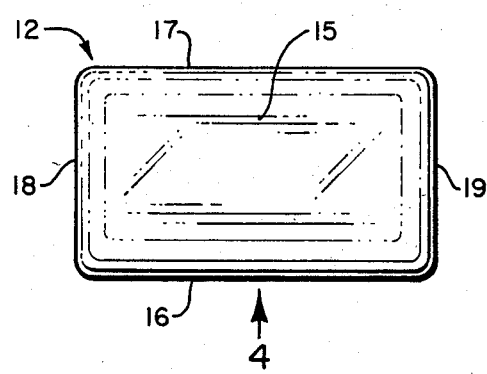
FIG. 3 is a top plan view of the staple looking in the direction of the arrow 3 of FIG. 2.

Referring to FIG. 2, there is shown an enlarged perspective view of the staple 12 of FIG. 1. This same staple is shown in plan, side, end, and bottom views in FIGS. 3, 4, 5 and 6 respectively and all of these views can be considered with respect to the following description.

As shown, the staple 12 comprises a rectangular top 15 having front and rear longitudinal edges 16 and 17 and left and right transverse edges 18 and 19.

Figure 4:
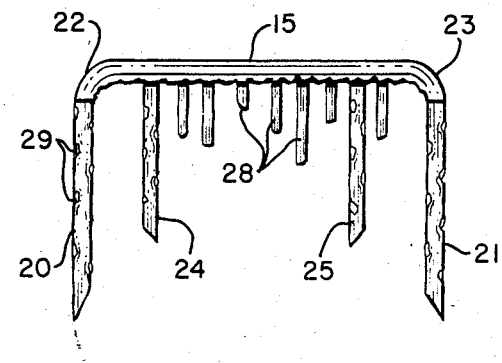
FIG. 4 is a side elevational view of the staple looking in the direction of the arrow 4 of FIG. 3.

As best shown in FIGS. 2 and 4, integrally formed downwardly depending front legs 20 and 21 are provided adjacent to the front corners 22 and 23 at opposite ends of the front longitudinal edge 16 of the top. As also clearly shown in FIGS. 2 and 4, there are provided integrally formed downwardly depending rear legs 24 and 25 spaced inwardly of the rear corners 26 and 27 at opposite ends of the rear longitudinal edge 17 of the top so as to be transversely offset from the front legs.

Figure 6:
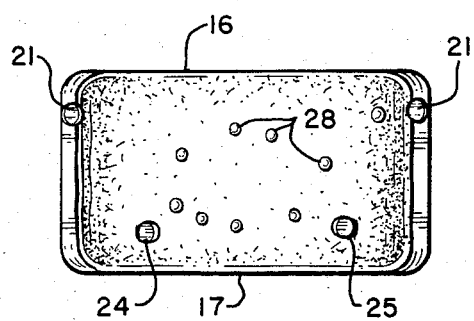
FIG. 6 is a plan view of the underside of the staple looking in the direction of the arrow 6 of FIG. 2.

With particular reference to FIGS. 2, 4 and 6, it will be noted that the under surface of the top 15 of the staple is roughened or rendered non-smooth and further includes a plurality of projections 28 of different lengths depending downwardly. These projections or spikes 28 in conjunction with the non-smooth under surface of the staple help greatly in retaining a tendon or ligament in place when the staple is driven into a bone all as will become clearer as the description proceeds.

With specific reference to FIG. 4, it will be noted that the rear legs 24 and 25 are shorter than the front legs 20 and 21. It is not necessary that these rear legs be shorter than the front legs but in certain types of staples there might be an advantage in providing shorter rear legs. For example, for certain bones it is easier to start the staple in the bone by only having to drive two prongs at one time. Also, where the bone presents an inclined surface where it is difficult to reach in certain environments, a better gripping might be accomplished with different length legs such as shown.

Also illustrated in FIG. 4 is a further feature in the form of scallops on opposite sides of the legs in a staggered array to increase frictional retention of the legs in the bone. Such scallops are shown for the leg 20 at 29 by way of example.

Figure 5:
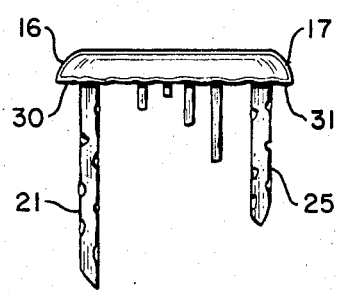
FIG. 5 is an elevational end view of the staple looking in the direction of the arrow 5 of FIG. 2.

Referring to FIG. 5, it will be noted that the front and rear legs as exemplified by the legs 21 and 25 are positioned inwardly of the front and rear longitudinal edges 16 and 17 of the top respectively to define longitudinal lips 30 and 31. These lips or flanges 30 and 31 are provided for engagement by an instrument when inserting and removing the staple all as will become clearer as the description proceeds.

Figure 7:
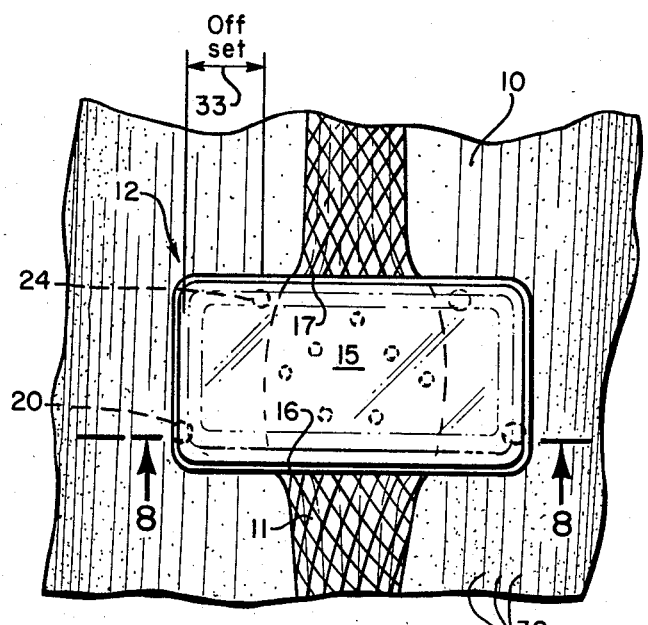
FIG. 7 is a plan view of the staple holding one end of a ligament to a bone surface.

Referring now to FIG. 7, there is shown a fragmentary plan view of the staple 12 of FIG. 1 in the bone 10. The faint vertical line indicated at 32 running from the bottom to the top of FIG. 7 depicts the cleavage planes or "grain" of the bone 10. It will be noted that the rectangular top 15 of the staple 12 bridges the bone grain so that the longitudinal edges 16 and 17 of the top are at right angles to the grain. As a consequence of the offset indicated by 33 of the rear legs from the front legs such as between the rear leg 24 and front leg 20 depicted in phantom lines, no two downwardly depending prongs or legs are aligned in the same cleavage plane or "grain" of the bone. Therefore, as described heretofore, the risk of splitting the bone when driving the legs of the staple into the bone is minimized.

Figure 8:
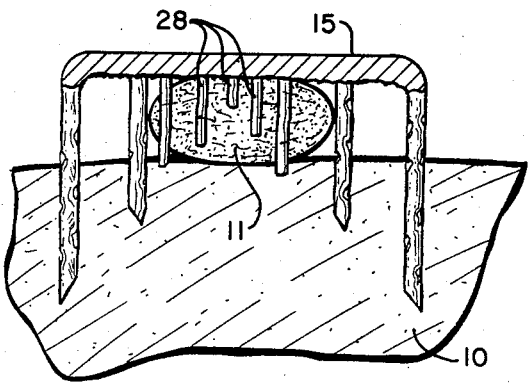
FIG. 8 is a fragmentary cross-section taken in the direction of the arrows 8—8 of FIG. 7.

With reference to both FIGS. 7 and 8, it will be clear that the tendon 11 is also bridged by the top 15, the engaged portion of the tendon or ligament being squashed into a more or less oval shape as indicated in FIG. 8. In this respect, it will be noted that the downwardly depending projections or spikes 28 will penetrate into the ligament 11, some of the spikes actually passing through the ligament to provide a very secure retention of the ligament to the staple. In addition, the roughened under surface of the top 15 increases the frictional engagement of the staple with the end of the ligament or tendon.

As already mentioned heretofore, the scallops on the legs will increase the frictional retention of the legs themselves in the bone 10.

Figure 9:
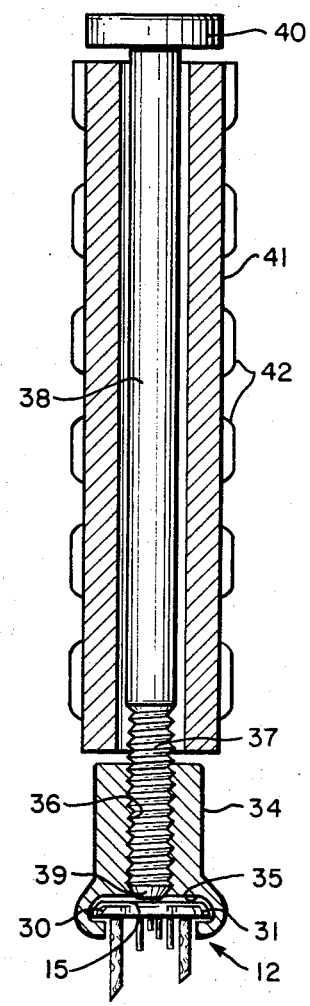
FIG. 9 is a side elevational view partly in cross section of an instrument for inserting the staple of the present invention into a bone; and, FIG. 10 is a side elevational view of the instrument of FIG. 9 appropriately adapted for removing the staple of the present invention from a bone.

Referring now to FIG. 9, there will be described an instrument for inserting the staple 12. Referring to the lower portion of FIG. 9, the instrument includes an elongated nut 34 having its lower end wall flaired out and thence inwardly on opposite sides to define a slot 35 dimension to receive the top 15 of the staple 12, the lips 30 and 31 of the staple being received in opposite ends of the slot as shown, the bottom of the slot being open so that the legs of the staple can extend downwardly.

The nut 34 has internal threads 36 receiving external threads 37 on the lower end of a shaft 38. The bottom of the shaft 38 engages the top 15 of the staple as at 39. It will be evident that by threading the shaft 38 further into the nut 34 a very tight gripping of the staple can be realized. The upper end of the shaft 38 terminates in a flat head 40.

Surrounding the shaft 38 is a sleeve 41 having surface projections 42 to provide a convenient gripping surface.

In operation, the shaft 38 is first separated from the nut 34 and the sleeve 41 received over the shaft 38. The lower threaded end 37 of the shaft 38 is then threaded into the nut 34 and the staple 12 is inserted in the slot 35. The lower end 39 of the shaft is threaded down against the top of the staple to lock it in place as described heretofore.

A surgeon can conveniently hold the instrument by means of the sleeve 41 and then tap the head 40 with a hammer to drive the staple 12 into a bone portion to secure the end of a ligament or tendon. With the staple in place, the threaded shaft 38 is rotated by the head 40 to lift the bottom 39 from the staple 35 and the nut 34 can then be slid off the end of the staple.

Figure 10:
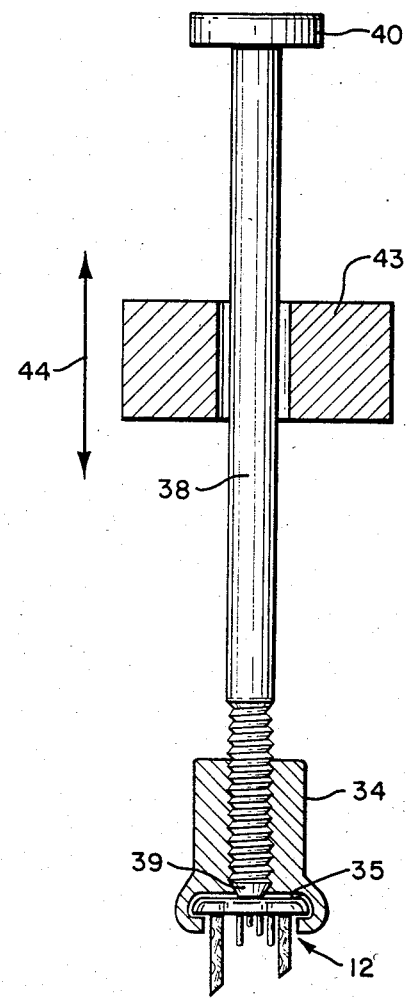

Referring to FIG. 10, the same instrument can be used slightly modified for removing the staple 12. The only difference in the instrument in FIG. 10 from that of FIG. 9 is the substitution of a weight 43 for the sleeve 41. Thus, when it is desired to remove the staple, the shaft 38 is initially separated from the nut 34 and rather than the sleeve 41, a weight 43 is positioned to surround the shaft 38. The threaded end of the shaft 38 is then received in the nut 34 so that the bottom of the shaft 39 is flush with the top of the slot 35. The end of the staple is then urged into the slot by sliding the slot over the staple end and when the staple is positioned in the slot, the shaft 38 is rotated to press down on the top of the staple and securely lock it relative to the nut 34.

After the foregoing securement has been achieved, the weight 43 is moved along the shaft 38 against the underside of the head 40 in rapid back and forth motions as indicated by the arrow 44. This tapping of the underside by the weight 43 will pull the staple from the bone.

From the foregoing description, it will now be evident that the present invention has provided a greatly improved orthopedic staple in which problems encountered with prior art staples have been essentially overcome.

Changes falling within the scope and spirit of this invention will occur to those skilled in the art. The orthopedic staple is therefore not to be thought of as limited to the specific embodiment set forth for illustrative purposes.

I claim:

1. An orthopedic staple comprising:
   (a) a rectangular top having front and rear longitudinal edges and left and right transverse edges;
   (b) integrally formed downwardly depending front legs adjacent to the front corners at opposite ends of the front longitudinal edge of said top; and
   (c) integrally formed downwardly depending rear legs spaced inwardly of the rear corners at opposite ends of the rear longitudinal edge of said top so as to be transversely offset from the front legs whereby bridging the bone grain so that said longitudinal edges of the top are at right angles to the grain minimizes the risk of splitting the bone when driving the legs of the staple into the bone.

2. A staple according to claim 1, including a plurality of projections of different lengths depending downwardly from the underside of said top for piercing and holding a tendon or equivalent tie secured by said staple to a bone portion.

3. A staple according to claim 1, in which said rear legs are shorter than said front legs.

4. A staple according to claim 1, in which each of the legs making up said front and rear legs are scalloped on opposite sides in a staggered manner to increase frictional retention of the leg in a bone.

5. A staple according to claim 1, in which said front and rear legs are positioned inwardly of the front and rear longitudinal edges of said top respectively to define longitudinal lips for engagement by an instrument when inserting and removing the staple.

6. A staple according to claim 1, in which the undersurface of said top is roughened to increase its frictional holding power.

7. An orthopedic staple for fixation of a tendon or other equivalent tie to a patient bone, comprising:
- a generally rectangular top having front and rear longitudinal edges, and left and right side edges;
- a pair of front legs formed integrally with said top and depending downwardly from respective positions generally adjacent the opposite ends of said front longitudinal edge;
- a pair of rear legs formed integrally with said top and depending downwardly from respective positions generally adjacent the opposite ends of said rear longitudinal edge, said rear legs being transversely offset relative to said front legs to minimize risk of bone splitting upon driving of said front and rear legs into the patient bone with said front longitudinal edge aligned generally at a right angle to the grain of the bone; and
- a plurality of projections of different lengths depending from said top for piercing and holding the tendon or equivalent tie to the patient bone.

8. An orthopedic staple for fixation of a tendon or other equivalent tie to a patient bone, comprising:
- a generally rectangular top having front and rear longitudinal edges, and left and right side edges;
- a pair of front legs formed integrally with said top and depending downwardly from respective positions generally adjacent the opposite ends of said front longitudinal edge;
- a pair of rear legs formed integrally with said top and depending downwardly from respective positions generally adjacent the opposite ends of said rear longitudinal edge, said rear legs being transversely offset relative to said front legs to minimize risk of bone splitting upon driving of said front and rear legs into the patient bone with said front longitudinal edge aligned generally at a right angle to the grain of the bone;
- a plurality of projections of different lengths depending from said top for piercing and holding the tendon or equivalent tie to the patient bone;
- said front legs being spaced rearwardly a short distance from said front longitudinal edge and said rear legs being spaced forwardly a short distance from said rear longitudinal edge to define respectively a front lip and a rear lip; and
- an instrument for driving said front and rear legs into the patient bone, said instrument including means for transversely sliding engagement with said front and rear lips.

* * * * *